(12) United States Patent
Livchak et al.

(10) Patent No.: US 9,645,009 B2
(45) Date of Patent: May 9, 2017

(54) ULTRAVIOLET MONITORING SYSTEMS, METHODS, AND DEVICES

(71) Applicant: OY HALTON GROUP LTD., Helsinki (FI)

(72) Inventors: Andrey V. Livchak, Bowling Green, KY (US); Chester Raczewski, Ontario (CA)

(73) Assignee: OY HALTON GROUP LTD., Helsinki (FI)

( * ) Notice: Subject to any disclaimer, the term of this patent is extended or adjusted under 35 U.S.C. 154(b) by 0 days.

(21) Appl. No.: 14/795,756

(22) Filed: Jul. 9, 2015

(65) Prior Publication Data

US 2015/0308890 A1    Oct. 29, 2015

Related U.S. Application Data

(63) Continuation of application No. 13/991,642, filed as application No. PCT/US2011/063344 on Dec. 5, 2011, now Pat. No. 9,119,891.

(Continued)

(51) Int. Cl.
*A61L 2/00* (2006.01)
*G01D 11/26* (2006.01)
(Continued)

(52) U.S. Cl.
CPC ............... *G01J 1/429* (2013.01); *A61L 9/20* (2013.01); *B01D 53/007* (2013.01);
(Continued)

(58) Field of Classification Search
CPC ..... A61L 9/00; A61L 9/20; B08B 3/04; F21V 19/006; H01K 3/00
(Continued)

(56) References Cited

U.S. PATENT DOCUMENTS 6,037,598 A    3/2000    Cicha
6,818,177 B1   11/2004   Turcotte
(Continued)

FOREIGN PATENT DOCUMENTS

CN    2855519 Y    1/2007
EP    1469290 A1   10/2004
(Continued)

OTHER PUBLICATIONS

International Search Report and Written Opinion dated Mar. 29, 2012, for International Application No. PCT/US2011/063344.
(Continued)

*Primary Examiner* — Monzer R Chorbaji
(74) *Attorney, Agent, or Firm* — Potomac Law Group, PLLC; Mark Catan (57) ABSTRACT

In embodiments, a control system for a UV air treatment system, especially one used for cleaning a fume stream such as in a kitchen exhaust system, detects a need for cleaning maintenance on the UV light source based on changes in light intensity. The system further detects the light intensity each time the UV light source is cleaned to determine if the drop in intensity after cleaning indicates that the UV light source should be replaced. The cleaning and replacement requirements are indicated automatically by a user interface.

20 Claims, 5 Drawing Sheets

Related U.S. Application Data (60) Provisional application No. 61/419,867, filed on Dec. 5, 2010.

(51) Int. Cl.
| | |
|---|---|
| *A62B 7/08* | (2006.01) |
| *G01N 23/00* | (2006.01) |
| *G01N 21/00* | (2006.01) |
| *G01J 1/42* | (2006.01) |
| *B01D 53/00* | (2006.01) |
| *F24C 15/20* | (2006.01) |
| *A61L 9/20* | (2006.01) |

(52) U.S. Cl.
CPC ..... *F24C 15/2021* (2013.01); *A61L 2209/111* (2013.01); *B01D 2259/4508* (2013.01); *B01D 2259/804* (2013.01)

(58) Field of Classification Search
USPC ..... 422/3, 24, 119, 121; 250/455.11, 453.11; 315/291, 313
See application file for complete search history.

(56) References Cited

U.S. PATENT DOCUMENTS

| | | | |
|---|---|---|---|
| 6,849,234 | B2 | 2/2005 | Lentz et al. |
| 7,318,856 | B2 | 1/2008 | Taylor et al. |
| 7,632,459 | B2 | 12/2009 | Lentz et al. |
| 7,705,744 | B2 | 4/2010 | Cutsforth |
| 2003/0170151 | A1 | 9/2003 | Hunter et al. |
| 2004/0224417 | A1 | 11/2004 | Wang |
| 2005/0238531 | A1 | 10/2005 | Trifu et al. |
| 2006/0130663 | A1 | 6/2006 | Joshi et al. |
| 2008/0095661 | A1 | 4/2008 | Kohler |
| 2010/0044319 | A1 | 2/2010 | Engel et al. |
| 2010/0225477 | A1 | 9/2010 | Livchak et al. |
| 2013/0093322 | A1 | 4/2013 | Borsuk et al. |

FOREIGN PATENT DOCUMENTS

| | | | | |
|---|---|---|---|---|
| JP | H57954 | | 3/1998 | |
| JP | 2006272184 | A | 10/2006 | |
| JP | 2008544829 | A | 12/2008 | |
| SE | WO 2007/008164 | * | 1/2007 | ............... A61L 9/20 |
| WO | WO 2007/008164 | A1 | 1/2007 | |

OTHER PUBLICATIONS

Combined Search and Examination Report issued Aug. 1, 2014, in Great Britain Patent Application GB1401970.7.
Memo concerning the Official Action for Mexican Patent Application No. MX/a/2013/006280, dated Aug. 25, 2014.
Memo concerning the Official Action for Mexican Patent Application No. MX/a/2013/006280, dated May 13, 2014.
Office Action issued Feb. 6, 2014, in Great Britain Patent Application GB1309792.8.
Office Action issued Oct. 31, 2014, in Chinese Patent Application No. 201180066864.8.
Patent Examination Report issued Apr. 13, 2015, in Australian Patent Application No. 2011338675.
Extended European Search Report issued Sep. 16, 2014, in European Application No. 11846235.7.
Notice of Reasons for Rejection issued Jun. 23, 2015, in Japanese Patent Application No. JP2013-543240.
Examination Report for Australian Patent Application No. 2011338675 issued Dec. 18, 2015.
Office Action for Japanese Patent Application No. 2013-543240 issued Apr. 26, 2016 with translation.
Office Action for Canadian Patent Application No. 2820243 issued Sep. 22, 2016.

* cited by examiner

ULTRAVIOLET MONITORING SYSTEMS, METHODS, AND DEVICES

CROSS REFERENCE TO RELATED APPLICATIONS

The present application claims the benefit of U.S. provisional application 61/419,867 for "Ultraviolet Monitoring Systems, Methods, and Devices," which was filed 5 Dec. 2010, the entirety of which is hereby incorporated by reference.

FIELD

The present invention is directed to maintenance of filtering systems that use ultraviolet light to degrade or sterilized contaminants.

BACKGROUND

The present invention is directed to maintenance of filtering systems that use ultraviolet light to degrade or sterilized contaminants.

SUMMARY

In embodiments, a control system for a UV air treatment system, especially one used for cleaning a fume stream such as in a kitchen exhaust system, detects a need for cleaning maintenance on the UV light source based on changes in light intensity. The system further detects the light intensity each time the UV light source is cleaned to determine if the drop in intensity after cleaning indicates that the UV light source should be replaced. The cleaning and replacement requirements are indicated automatically by a user interface.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

In some applications, ultraviolet (UV) sources such as lamp bulbs tend to get dirty. For example, in one application, in kitchen exhaust systems, oil droplets appear in grease smoke from kitchen, such as a commercial kitchen. Grease filters are not entirely effective to remove grease droplet making up the majority of the pollutants in such smoke because they only capture the larger droplets. UV can be used to degrade much finer droplets making up grease smoke. To provide a treatment, UV lamps must be exposed to grease smoke. However, even fine particles tend to stick to surfaces of the UV lamps reducing their output.

The present invention is an intelligent detection and maintenance advisor device that monitors the intensity of UV sources over time and indicates to maintenance operators when to clean UV sources that have become dirty and when to replace the sources based on a historical record of the detected intensity.

Figure 1:
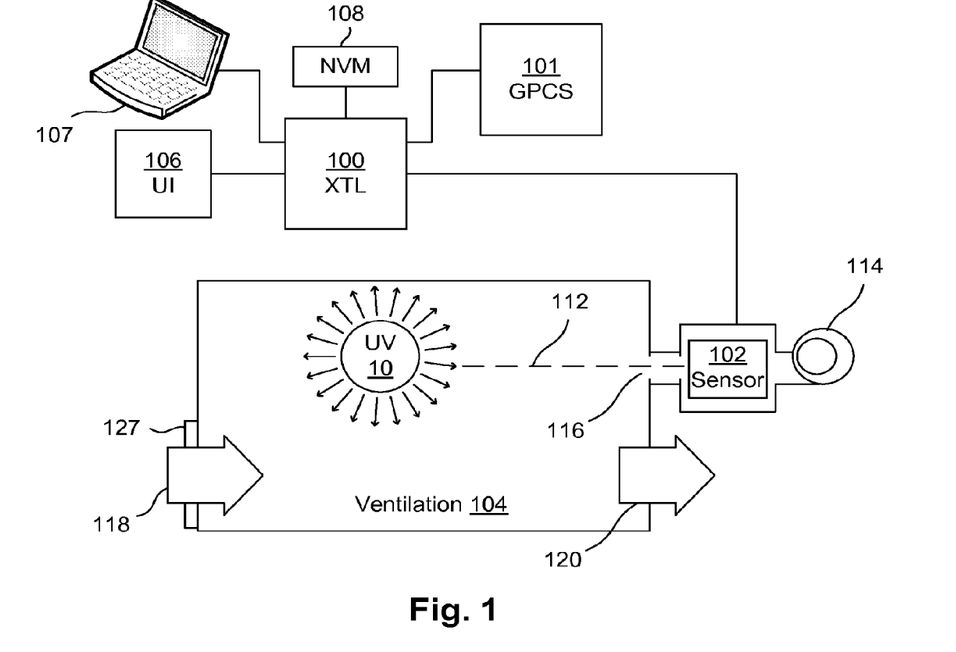
FIG. 1 shows an ultraviolet air treatment system according to embodiments of the disclosed subject matter.

Referring to FIG. 1, a ventilation treatment device 104 receives polluted air 118. The polluted air flows through the ventilation treatment device 104 where the polluted air 118 is exposed to light from a UV source 10. The treated air 120 then exist the ventilation treatment device 104. A sensor 102 continually monitors the intensity of light from the UV source 10 by detecting some of the light 112 that passes to the sensor 102. In an embodiment, the sensor 102 is protected from contamination by a flush stream of clean air 116 forced by a fan 114 into the ventilation treatment device 104, thereby preventing pollutants in the ventilation treatment device 104 from accumulating on the sensor 102.

Figure 2:
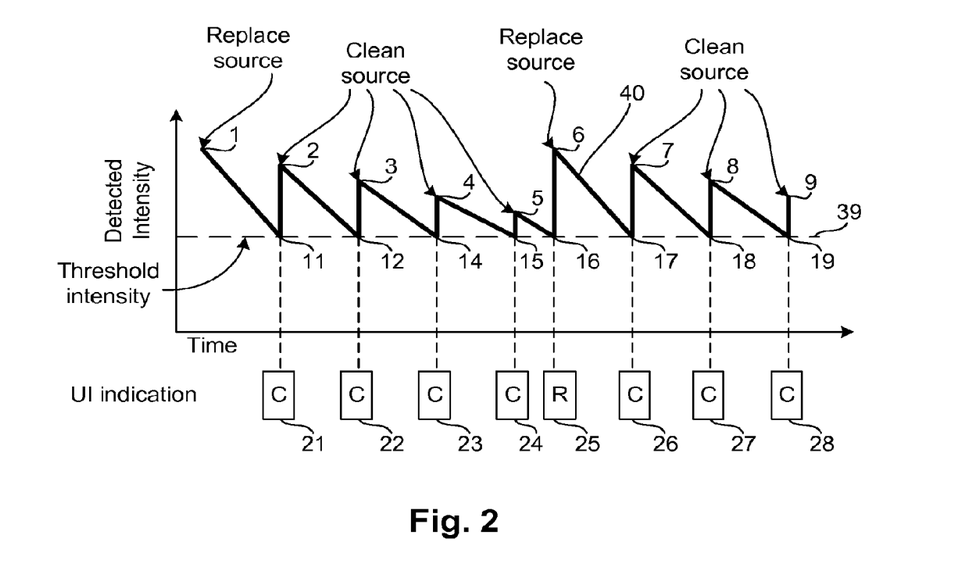
FIG. 2 illustrates a time series of intensity measurements with corresponding control system output mapped thereto according to embodiments of the disclosed subject matter.

A controller 100 regularly polls the sensor 102 and creates a record, which is stored in a non-volatile memory 108 (e.g., a flash memory), of readings from the sensor 102. Referring now also to FIG. 2, a (sawtooth-shaped) curve 40 shows a history of the light intensity indicated by the sensor 102 according to axes of intensity versus time. A new UV source 10 generates an output as indicated at 1. When light from the UV source falls below a threshold intensity 39, as indicated by point 11, an indication is generated by the controller 100 to clean the UV source 10. The new UV source may be the result of a change of an expired UV source or more than one expired UV source. The indication may be output on a user interface 106, for example, an LCD display or a lamp labeled "Clean." The comparison between a stored threshold level and the detected level may be made by the controller 100. The threshold level may be obtained upon replacement of the UV source 10 from a percentage calculation made by the controller, for example the threshold may be 50% of the intensity of the new UV source 10.

The cleaning of the UV source 10 results in a higher intensity as indicated at 2, but the intensity is lower than the intensity 1 of a new lamp as indicated. As the cleaned UV source 10 is used its intensity falls again to the threshold level 39 as indicated at 12 whereupon the signal to clean is again generated as indicated at 22. The cycle repeats with an indication to clean being output at 23 and 24 corresponding to intensity points 14 and 15. The corresponding clean intensity levels, 3, 4, and 5 progressively diminish with time. At the time when the threshold level is again met at point 16, a indication 26 to replace the UV source is output at which time the intensity is restored to the level at point 6. In addition, the time between intensity threshold crossings may diminish progressively as well providing an alternative indicator of the need to replace the UV source.

The indication to clean may be determined by the intensity of the most recent new cycle, for example the percentage difference between the stored intensity value 2 and threshold intensity 39. If the difference exceeds a predetermined amount, the controller 100 generates a signal to clean. If it is below this predetermined level the indication to replace the UV source, e.g., a bulb, is generated. The cycle then repeats through commands 26, 27, 28 and so on coinciding with dirty points 18, 18, 19 to restore output to levels at clean points 7, 8, and 9. It should be clear that this profile can be repeated indefinitely. The predetermined intensity values may be stored in the nonvolatile storage 108. Other data than the intensity values can be stored. For example, the elapsed time since a cleaning indication may be stored.

When a cleaning or replacement indication is output, the system may wait for an indication that the maintenance operation has been performed. For example, after cleaning the UV source, a command may be input by a user through the user interface to reset the maintenance indication currently being output (clean or replace). Alternatively, the system may detect the change in intensity and reset itself. For example, an upper threshold may be defined which, when exceeded, indicates the UV source has been properly cleaned. Another upper threshold, higher than the other, may be defined indicating the UV source has been properly replaced. In response to one or both, the system may update the status of the UV source to a cleaned or replaced UV source. Another way the controller may be configured to reset the status of the UV source is to detect a positive change in the intensity of greater than a predefined amount. So rather than having a particular threshold intensity that the light source exceeds, the reset is indicated when the positive change in intensity since a last recorded intensity is greater than a predefined amount.

Figure 3:
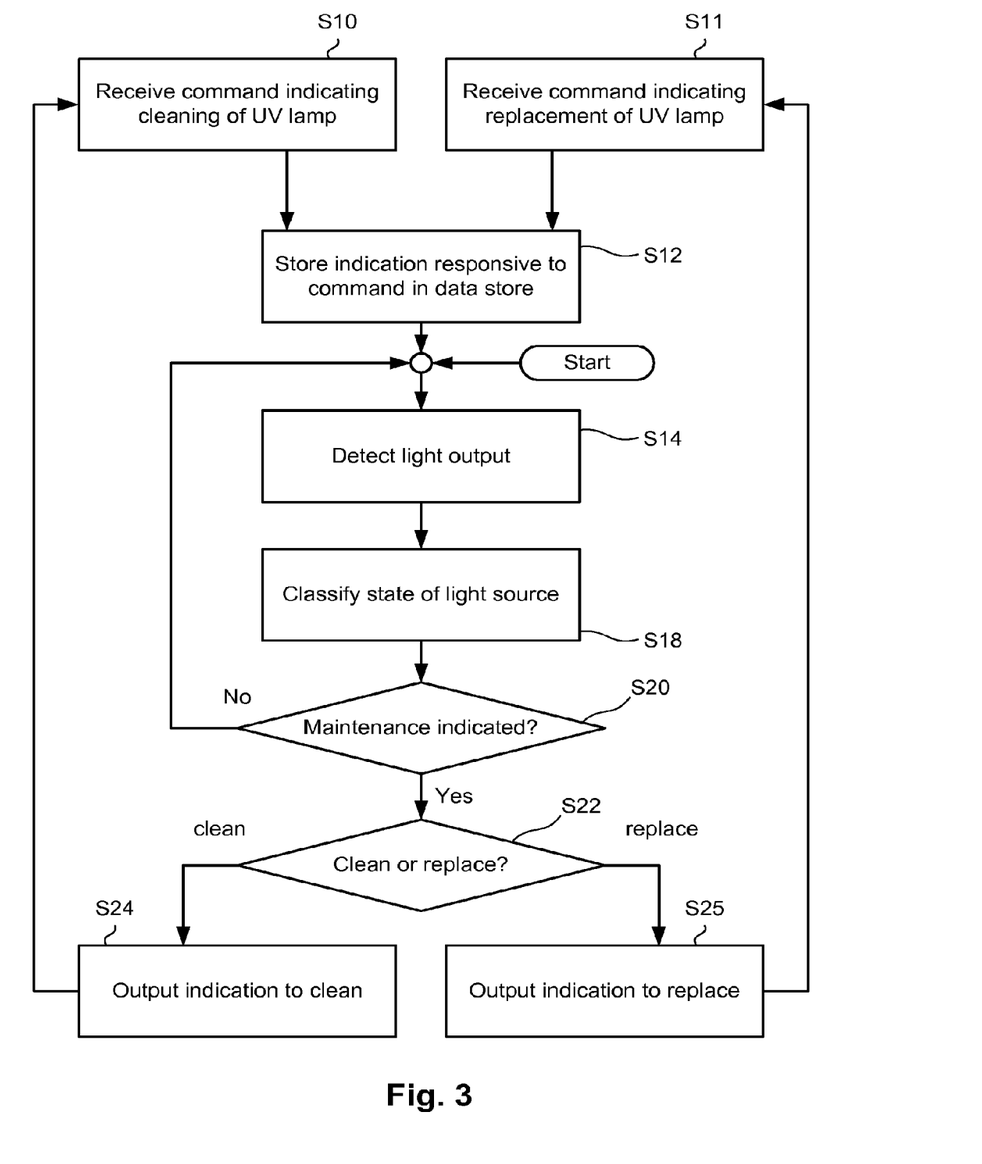
FIG. 3 shows a flow chart of a procedure for indicating maintenance requirements for a UV light source according to embodiments of the disclosed subject matter.

Referring now to FIG. 3, a flow chart shows a procedure for outputting maintenance steps of cleaning and replacing UV light sources. Light output from a UV source is detected during normal operation of the ventilation system at S14. At S18, from the current level of the light output measured or from an historical trend the need for either a cleaning operation or a replacement operation is determined according to any of the criteria described elsewhere in the present specification. At S20, if a maintenance output is indicated, control proceeds to S22 otherwise it loops back to S14. At S22, the type of control output is determined and the corresponding output is generated at S24 or S25, respectively after which control proceeds to S10 or S11, respectively as indicated. At S10 and S11, the completion of the respective maintenance action is detected, or a command received indicating its completion, and an indication stored at S12 that the maintenance is done. The S12 operation may include storing a value of the intensity after a cleaning, or other data responsive thereto, for purposes of determining whether a replacement operation is, or will be, required according to criteria of any of the applicable embodiments described herein.

Figure 4:
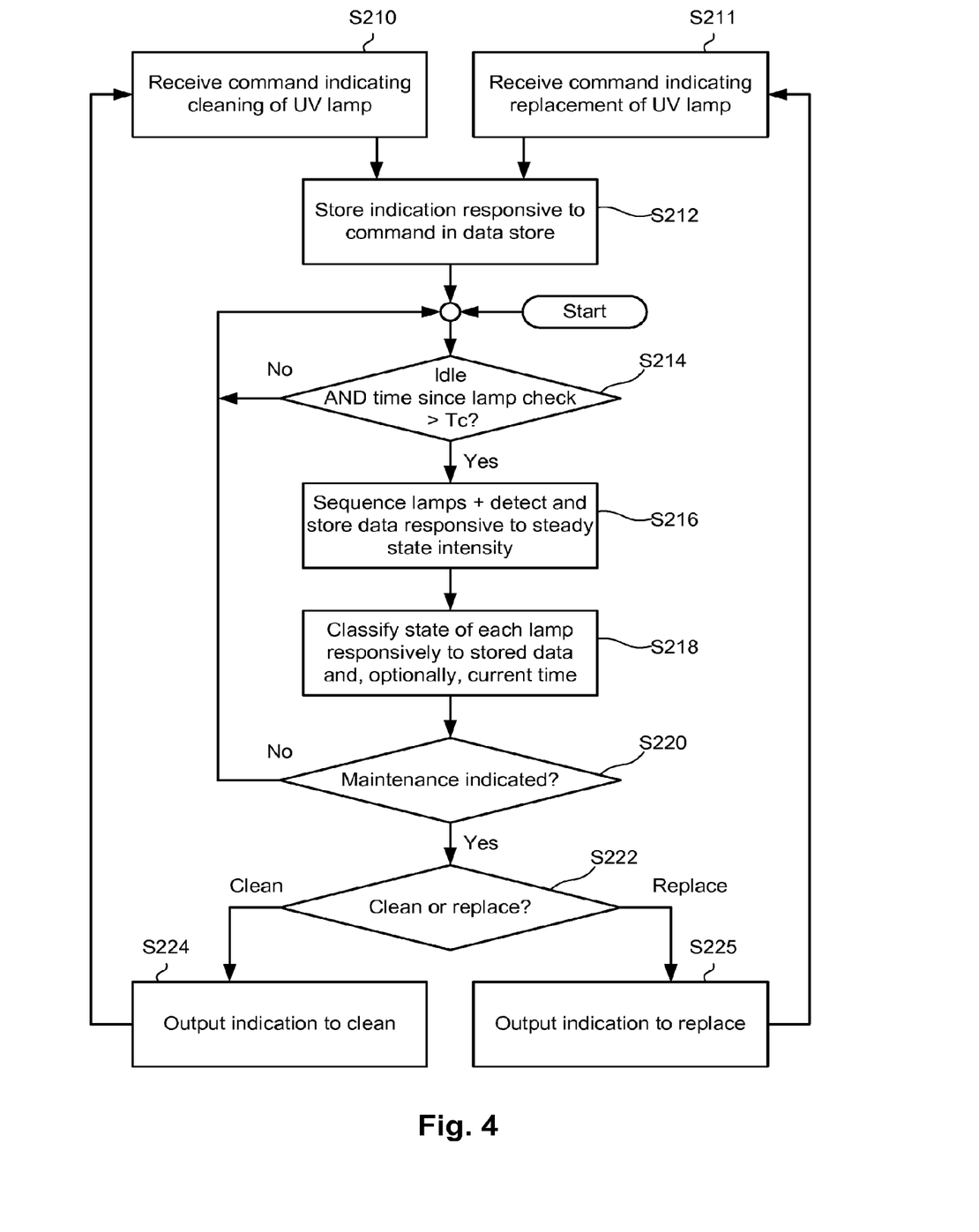
FIG. 4 shows a flow chart of a procedure for indicating maintenance requirements for a UV light source according to further embodiments of the disclosed subject matter.

Referring now to FIG. 4, a flow chart shows a further procedure for outputting maintenance steps of cleaning and replacing UV light sources. The controller determines whether the elapsed time since a prior lamp check is beyond predefined interval TC at S214. If not the control loops, otherwise at S216, a procedure is performed in which the light output from each lamp of multiple lamps is performed to acquire the output of each lamp. At S218, the status of each lamp is determined according to criteria discussed in the present specification. If maintenance output indicator is required as determined at S220, control proceeds to S222 otherwise it loops back to S214. At S222, the type of control output is determined and the corresponding output is generated at S224 or S225, respectively after which control proceeds to S210 or S211, respectively as indicated. At S210 and S211, the completion of the respective maintenance action is detected, or a command received indicating its completion, and an indication stored at S212 that the maintenance is done. The S212 operation may include storing a value of the intensity after a cleaning, or other data responsive thereto, for purposes of determining whether a replacement operation is, or will be, required according to criteria of any of the applicable embodiments described herein.

Figure 5:
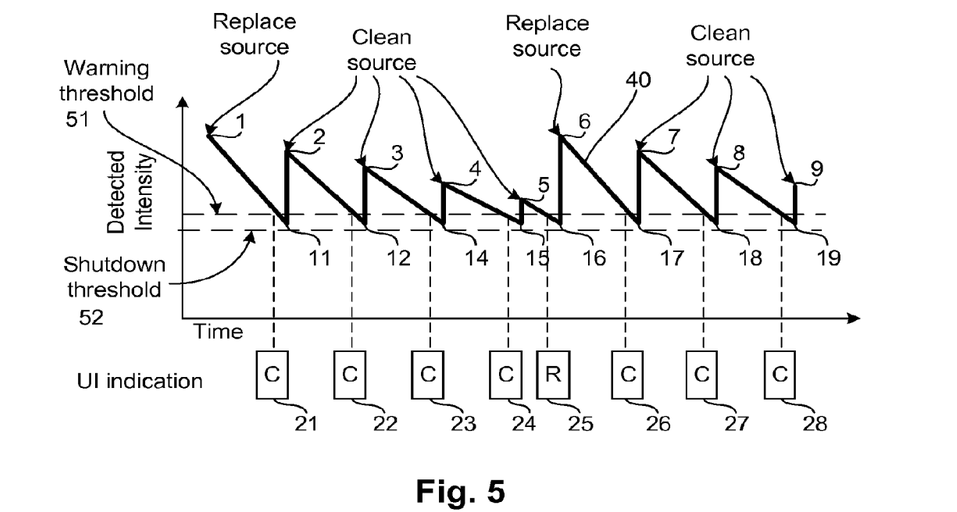
FIG. 5 is a variation of FIG. 2 illustrating a different scheme for responding to intensity level changes.

Referring to FIG. 5, the system may allow operation of the lamp if a cleaning operation is required, except that the output of the user interface may continue to indicate a need for cleaning. The system may also prevent operation of the hood if there is no response after an output of a cleaning indication. The system may provide a grace period of a predefined period of time or a predefined number of startups of the ventilation system after the first output of an indication to clean or replace. The grace period may be different for each of the indications, namely clean or replace. In an embodiment, the system provides a warning indication of a need for clean or replace after passing a first threshold intensity 51 but only begin enforcing the maintenance operation by preventing the use of the ventilation system after the intensity drops through a second, lower threshold 52.

Figure 6:
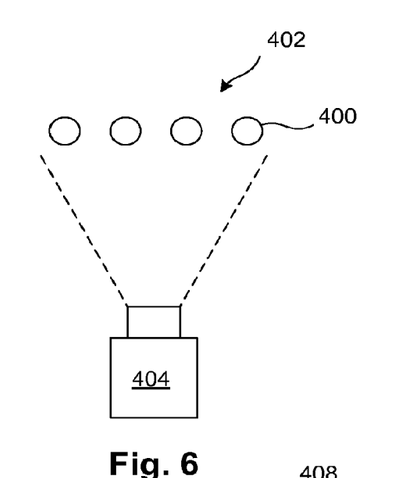
FIG. 6 illustrates an imaging system for acquiring intensity data from a UV light source including multiple lamps.
Figure 7:
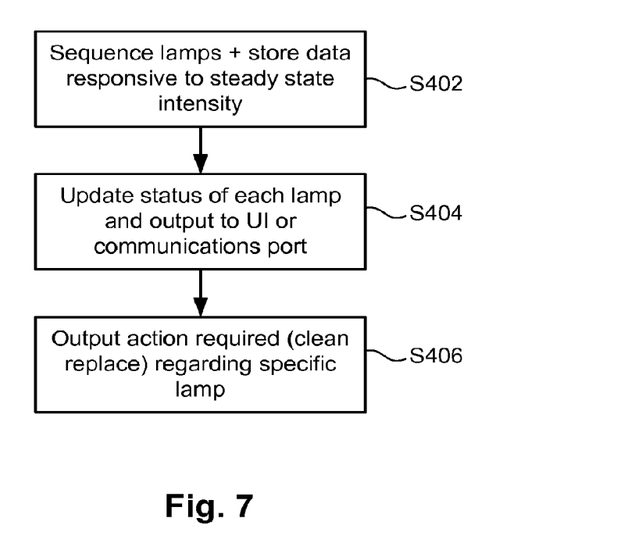
FIG. 7 is a flow chart showing a portion of a procedure that may be used in any of the embodiments described.
Figure 8:
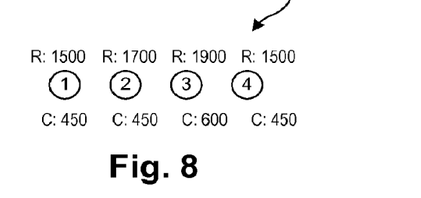
FIG. 8 shows an output display example according to embodiments of the disclosed subject matter.

Referring to FIGS. 6 and 7, in any of the embodiments, the condition of each lamp 400 in an array 402 is imaged simultaneously or individually by an imaging device such as a camera. In this way, the intensity of each lamp can be acquired separately by processing the image and segmenting the light intensity of each lamp 400 respectively. As indicated at S404 and S406, in response, the status (here indicated as a predicted time till next required action) of each lamp can be listed on an output as a separate indication. For example, a schematic of FIG. 8 can be generated by a UI with predicted hours till next cleaning or predicted hours to replacement indicated for each lamp 400 as indicated at 408. Alternatively the data for the predicted time till indicated action can be listed in a data packet transmitted to a central controller as discussed above.

In any of the embodiments, instead of an output of an indication of a need to clean or replace, the control system can generate a prediction of when the lamps will next need to be cleaned and when they will next need to be replaced. Such a system may provide an output indication of both pieces of information. This information may be output as a control signal to a central ventilation monitoring system so that the controller for the UV treated system does not need to have its own output display or other output terminal. An Internet-connected control system can automatically order a set of replacement sources when a predefined time is indicated between the current time and the predicted time for replacement. This feature may be implemented by providing the controller and software that runs on a general purpose computer (FIG. 1, 107) or one that is connected to a general control system (FIG. 1, GPCS 101). The latter may be a part of, for example, a control system for a commercial kitchen or the HVAC system for a building and may use a standard protocol to output status information and/or recommended actions to the general purpose control system.

In any of the foregoing embodiments, the status of the UV light source may be inferred from other detected data. For example, the surface pattern of light of a lamp may be compared in terms of uniformity or in terms of a particular pattern of intensity over its surface such that the light distribution, rather than the overall intensity indicates the condition of the lamp. For example, an irregular pattern of light or one or light blocking "blobs" may be imaged by a suitable camera to indicate fouling by fumes or aerosols in the ventilation air, for example.

In any of the embodiments, the control system may be configured to detect other anomalies in the output of the UV light source. The decay rate of intensity fo the UV source may provide a useful indicator of the operating status of a filter (indicated at 127 in FIG. 1) upstream of the UV sources. For example, in a kitchen exhaust system, typically grease filters are used to trap particulates before further treatment by a UV source. If the grease filters are left out, not properly installed, or functioning poorly, the rate of fouling of the UV source may indicate this. This attending abnormally high rate of diminution of intensity may be indicated in any of the described systems according to any of the information output schemed described above or elsewhere.

In any of the disclosed embodiments, the failure of a lamp or power supply may be detected and indicated by any of the disclosed UI systems as well as diagnosis of performance and maintenance actions as discussed.

In a representative operating scenario, a ventilation system is started after UV sources that were just replaced. The ventilation system is operated continuously or in multiple cycles (such as multiple mealtime cycles of operation of a kitchen or diurnal cycles of an office ventilation system). At one or more times during each operating cycle or at times during continuous operation of a ventilation system that does not cycle but runs continuously, the UV source intensity is acquired (or otherwise acquired for example, the light sources may be imaged according to the respective embodiment). In embodiments, the UV source or each element (e.g., lamp) may have a predicted status, for example, representable as operating hours till cleaning and operating hours till replacement. These values may be updated based on historical trends in the intensity data. In other embodiments, the intensity data may be stored in original for and used at any selected time to generate a prediction or "action required" output such as an indication to clean or an indication to replace one lamp or a single UV source. Instead of estimated operating time to next cleaning and/or replacement, the elapsed time, based on predicted usage, may be calculated and output.

In the operating scenario, a succession of status indications may be generated responsively to a request or automatically. For example, the estimated time to next cleaning may be continuously output or output responsively to the crossing of a threshold (e.g., threshold 51 of FIG. 5) or output according to an expected time until the need for the maintenance operation.

Figure 9:
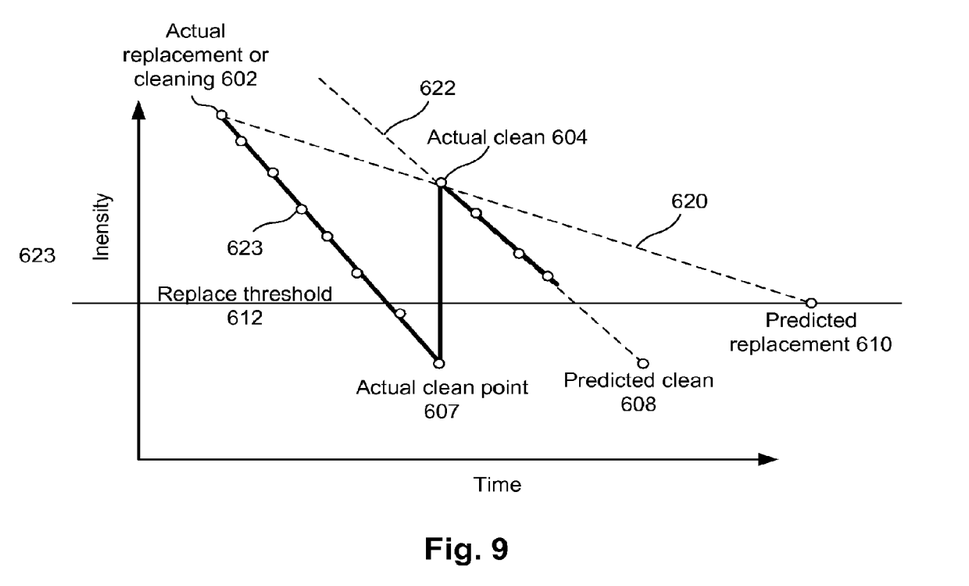
FIG. 9 illustrates a scheme for estimating cleaning points and replacement points for maintaining UV light sources.

Referring to FIG. 9, estimating status or maintenance events by the controller may be done using any of a variety of techniques. For example, the expected time until a maintenance operation may be derived from a line of best fit between respective points. In FIG. 9, two points one representing intensity after an actual cleaning or replacement 602, and another representing intensity after an actual cleaning 604 allow a line of best fit (if there were more points it would be a line of best fit according least squares or other scheme) to be drawn and extrapolated to a predicted threshold 612 for replacement, thereby yielding a predicted replacement point 610. In the same way multiple intensity measurements occurring at various times during operation or during calibration periods 623 can be extrapolated to an predicted cleaning point 608. The time scale may be operating hours or elapsed actual time.

According to embodiments, the disclosed subject matter includes a method of maintaining an ultra-violet air treatment system. The method includes detecting an intensity of at least one ultraviolet light source at successive points in time during operation thereof in an air treatment system. The method further includes applying signals representing the intensity to a controller and storing data responsive to the detected intensities in a data store. The controller, at a first time, on a user output terminal, generates an indication that the at least one ultraviolet light source requires cleaning. The controller, at a second time, on the user output terminal, generates an indication that the at least one ultraviolet light source requires replacement. The controller receives a maintenance indication where the maintenance indication is a signal indicating at least one of the completion of a cleaning of the ultraviolet light source and a replacement of the at least one ultraviolet light source. The generating operation that generates an indication that the at least one ultraviolet light source requires cleaning is responsive to the maintenance indication and stored data responsive to the intensity of the at least one ultraviolet light source immediately after maintenance indication.

According to embodiments, the disclosed subject matter includes a method of maintaining an ultra-violet air treatment system. The method includes detecting an intensity of at least one ultraviolet light source at successive points in time during operation thereof in an air treatment system. The method further includes applying signals representing the intensity to a controller and storing data responsive to the detected intensities in a data store. The controller, at a first time, on a user output terminal, generates an indication that the at least one ultraviolet light source requires cleaning. The controller, at a second time, on the user output terminal, generates an indication that the at least one ultraviolet light source requires replacement. The controller receives a maintenance indication where the maintenance indication is a signal indicating at least one of the completion of a cleaning of the ultraviolet light source and a replacement of the at least one ultraviolet light source. The generating an indication that the at least one ultraviolet light source requires replacing is responsive to the maintenance indication and stored data responsive to the intensity of the at least one ultraviolet light source at multiple points in time such that the indication that the ultraviolet lamp requires replacing is generated if multiple maintenance indications have been received by the controller indicating cleaning of the at least one ultraviolet light source.

According to embodiments, the disclosed subject matter includes a method of maintaining an ultra-violet air treatment system. The method applies to a system that includes a controller where the controller has at least one sensor and an output device and is configured to perform the method. The method includes detecting an intensity of at least one ultraviolet light source at successive points in time. The method further includes receiving an indication that the at least one ultraviolet light source has just been cleaned. When the detected intensity is above a first threshold upon a first detecting after a receiving, the controller outputs no maintenance indication. When the detected intensity is below the first threshold upon a first detecting after a receiving, the controller outputs a maintenance indication indicating to replace the ultraviolet light source. When the detected intensity is below a second threshold upon a detecting subsequent to a first detecting after a receiving, the controller outputs a maintenance indication indicating to clean the ultraviolet light source.

In the above method, the first threshold may correspond to a lower intensity than the first threshold.

According to embodiments, the disclosed subject matter includes a method of maintaining an ultra-violet air treatment system, the system including a controller. The controller has at least one sensor and an output device and is configured to perform the method which includes detecting an intensity of at least one ultraviolet light source at successive points in time. The method further includes receiving an indication that the at least one ultraviolet light source has just been cleaned. When the detected intensity is above a threshold upon a first detecting after a receiving, the controller outputs no maintenance indication. When the detected intensity is below the threshold upon a first detecting after a receiving, the controller outputs a maintenance indication indicating to replace the ultraviolet light source. When the detected intensity is below the threshold upon a detecting subsequent to a first detecting after a receiving, the controller outputs a maintenance indication indicating to clean the ultraviolet light source.

In any of the methods, the at least one ultraviolet light sources may include multiple lamps in a ventilation plenum. The at least one ultraviolet light sources may include multiple lamps in a chamber downstream of at least one kitchen exhaust hood. The controller may include a programmable digital controller.

According to embodiments, the disclosed subject matter includes a system including an exhaust hood and a controller adapted for performing any of the methods described herein. According to embodiments, the disclosed subject matter includes a controller configured for performing any of the recited methods. According to embodiments, the disclosed subject matter includes a computer readable medium having instructions recorded thereon for performing any of the above recited methods.

The foregoing medium may include instructions wherein the air treatment system includes a kitchen exhaust system. The foregoing controller may be configured for operation in a system that includes a kitchen exhaust system. The air treatment system may include a kitchen exhaust system in any of the foregoing embodiments. The maintenance indication may include an estimate of time until the maintenance is required.

According to embodiments, the disclosed subject matter includes a method of maintaining an ultra-violet air treatment system. The method includes detecting light output from an ultraviolet light source at multiple points in time. From a first trend in the data, the data representing multiple instances of the detecting, the a required first maintenance action is determined to elevate the light output from the light source and outputting an indication of the required maintenance action. The method further includes detecting a performance of the first maintenance action. From a second trend in the data representing multiple instance of the detecting in combination with the detecting a performance of the first maintenance event the method determines a required second maintenance action and outputting an indication of a need for the second maintenance action responsively thereto.

The detecting a performance may include detecting a change in light output indicating the completion of the first maintenance action. The first maintenance action may include cleaning the ultraviolet light source. The second maintenance action may include replacing or repairing the ultraviolet light source. The outputting may include displaying a message on a user interface indicting, respectively, the need for the first and second maintenance actions. The detecting a performance may include receiving a user input indicating the completion of the first maintenance action.

According to embodiments, the disclosed subject matter includes a method of maintaining an ultra-violet air treatment system. The method includes detecting light output from an ultraviolet light source at multiple points in time and when the light output drops to a first level, outputting an indication that the ultraviolet light source needs to be cleaned. In response to a detection that the ultraviolet light source has been cleaned and a detection of a light output below a second level at a time approximately contemporaneous with the detection that the ultraviolet light source has been cleaned, an indication that the ultraviolet light source needs to be changed is output by the controller. The outputting of an indication that the ultraviolet light source needs to be changed may be performed in response to a subsequent to the time approximately contemporaneous with the detection that the ultraviolet light source has been cleaned. The at least one ultraviolet light sources may include multiple lamps in a ventilation plenum. The at least one ultraviolet light sources may include multiple lamps in a chamber downstream of at least one kitchen exhaust hood. The controller may be a programmable digital controller.

According to embodiments, the disclosed subject matter includes a system including an exhaust hood and a controller adapted for performing any of the methods or a controller configured for performing any of the methods, or a computer readable medium having instructions recorded thereon for performing any of the methods.

It will be appreciated that the modules, processes, systems, and sections described above can be implemented in hardware, hardware programmed by software, software instruction stored on a non-transitory computer readable medium or a combination of the above. For example, a method for indicating a maintenance operation can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of ventilation control and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, systems, methods, and devices monitoring an ultraviolet air treatment apparatus. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

The invention claimed is:

1. A method of maintaining an ultra-violet air treatment system, the method comprising:
   detecting light output from an ultraviolet light source at multiple points in time;
   providing light output data from said detecting to a controller of the ultra-violet air treatment system;
   from a first trend in the data representing multiple instances of the detecting light, determining by the controller a first maintenance action required to elevate the light output from the light source and outputting an indication of the first maintenance action;
   detecting by the controller a performance of the first maintenance action; and
   from a second trend in the data representing multiple instances of the detecting the light in combination with the detecting the performance of the first maintenance action, determining by the controller a second maintenance action and outputting an indication of a need for the second maintenance action responsively thereto.

2. The method of claim 1, wherein the detecting a performance of the first maintenance action includes detecting a change in light output indicating completion of the first maintenance action.

3. The method of claim 2, wherein the first maintenance action includes cleaning the ultraviolet light source.

4. The method of claim 3, wherein the second maintenance action includes replacing or repairing the ultraviolet light source.

5. The method of claim 4, wherein the outputting includes displaying a message on a user interface of a kitchen exhaust system indicating, respectively, the need for the first and second maintenance actions.

6. The method of claim 2, wherein the second maintenance action includes replacing or repairing the ultraviolet light source.

7. The method of claim 6, wherein the outputting includes displaying a message on a user interface of a kitchen exhaust system indicating, respectively, the need for the first and second maintenance actions.

8. The method of claim 1, wherein the first maintenance action includes cleaning the ultraviolet light source.

9. The method of claim 8, wherein the second maintenance action includes replacing or repairing the ultraviolet light source.

10. The method of claim 9, wherein the outputting includes displaying a message on a user interface of a kitchen exhaust system indicating, respectively, the need for the first and second maintenance actions.

11. The method of claim 8, wherein the detecting a performance includes receiving a user input indicating the completion of the first maintenance action.

12. The method of claim 1, wherein the second maintenance action includes replacing or repairing the ultraviolet light source.

13. The method of claim 12, wherein the detecting a performance includes receiving a user input indicating the completion of the first maintenance action.

14. The method of claim 1, wherein the outputting includes displaying a message on a user interface of a kitchen exhaust system indicating, respectively, the need for the first and second maintenance actions.

15. The method of claim 1, wherein the detecting a performance includes receiving a user input indicating the completion of the first maintenance action.

16. A method of maintaining an ultra-violet air treatment system, the method comprising:
   detecting light output from an ultraviolet light source at multiple points in time;
   when the light output drops to a first level, outputting an indication that the ultraviolet light source needs to be cleaned; and
   in response to a detection that the ultraviolet light source has been cleaned and a detection of a light output below a second level at a time approximately contemporaneous with the detection that the ultraviolet light source has been cleaned, outputting an indication that the ultraviolet light source needs to be changed.

17. The method of claim 16, wherein the outputting an indication that the ultraviolet light source needs to be changed is performed subsequent to the time approximately contemporaneous with the detection that the ultraviolet light source has been cleaned.

18. The method of claim 17, wherein the ultraviolet light source includes multiple lamps in a ventilation plenum.

19. The method of claim 18, wherein the ultraviolet light source includes multiple lamps in a chamber downstream of at least one kitchen exhaust hood.

20. The method of claim 19, wherein a programmable digital controller receives results of said detecting the light output and determines that the light source needs to be cleaned based on the received results.

* * * * *